United States Patent [19]

Syrier

[11] 4,254,280
[45] Mar. 3, 1981

[54] CYCLOPROPANE DERIVATIVE

[75] Inventor: Johannes Syrier, Amsterdam, Netherlands

[73] Assignee: Shell Oil Company, Houston, Tex.

[21] Appl. No.: 96,870

[22] Filed: Nov. 23, 1979

Related U.S. Application Data

[62] Division of Ser. No. 55,854, Jul. 9, 1979.

[30] Foreign Application Priority Data

Jul. 19, 1978 [GB] United Kingdom ............... 30335/78
Jul. 19, 1978 [GB] United Kingdom ............... 30336/78
Jul. 19, 1978 [GB] United Kingdom ............... 30339/78
Jul. 19, 1978 [GB] United Kingdom ............... 30373/78

[51] Int. Cl.$^3$ ........................................... C07C 69/145
[52] U.S. Cl. ................................... 560/231; 560/238; 568/303; 568/347; 260/345.2
[58] Field of Search ............................... 560/231, 238

[56] References Cited

U.S. PATENT DOCUMENTS

| 3,708,528 | 1/1973 | Mukherjee et al. .................. 560/231 |
| 4,024,163 | 5/1977 | Elliott et al. ....................... 260/347.4 |

FOREIGN PATENT DOCUMENTS

1413419  11/1975  United Kingdom .

OTHER PUBLICATIONS

Houken-Weyl, Methoden der Organischen Chemie, VII, Part 1, pp. 423–428, (1952), VIII, pp. 516–526 and 543–550, (1952).
Ghisalberti et al., Tetrahedron, 29, 403–412, (1973).
Lavielle et al., Bull. Soc. Chim. Fr., No. 6, pp. 2047–2053, (1971).
Combret et al., Tetrahedron Letters, 15, pp. 1035–1038, (1971).
Ried et al., Ann. der Chemie, 679, 51–55, (1964).
Castro et al. I, Bull. Soc. Chim. Fr., No. 8, 2770–2773, (1969).
Castro et al. II, C. R. Acad. Sci. Paris, 268(11), Series C., 1067–1069, (1969).
Salmond, Tetrahedron Letters, 1977, No. 14, 1239–1240, (1977).

*Primary Examiner*—Jane S. Myers

[57] ABSTRACT

2-(2-Hydroxy-3-oxobutyl)-3,3-dimethylcyclopropanecarbaldehyde and certain derivatives thereof, such as 1-[2-(2,2-dihalovinyl)-3,3-dimethylcyclopropyl]-3-oxo-2-butyl acetate, are useful intermediates for the preparation of dihalovinyl-type pyrethroid esters.

3 Claims, No Drawings

CYCLOPROPANE DERIVATIVE

This is a division, of application Ser. No. 55,854, filed July 9, 1979 pending.

BACKGROUND OF THE INVENTION

Field of the Invention: The present invention is directed to new cyclopropane derivatives, their preparation, and to their use in the preparation of certain synthetic pyrethroids.

SUMMARY OF THE INVENTION

The present invention is directed to a new chemical compound 2-(2-hydroxy-3-oxobutyl)-3,3-dimethylcyclopropanecarbaldehyde having the formula I

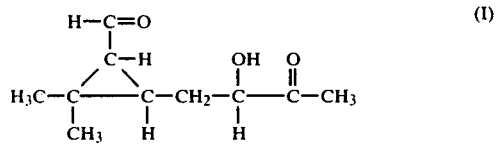

which is useful as an intermediate in the preparation of pyrethroid esters of 2-(2,2-dihalovinyl)-3,3-dimethylcyclopropanecarboxylic acid. Compound I has two asymmetric carbon atoms in the cyclopropane ring and, therefore, can have the (1R,cis), (1R, trans), (1S,cis) or (1S,trans) configuration. The nomenclature used herein to describe the spatial configuration has been defined by M. Elliott et al., *Nature,* 248, pages 710-1 (1974).

The invention also provides a process for the preparation of 2-(2-hydroxy-3-oxobutyl)-3,3-dimethylcyclopropanecarbaldehyde, which comprises hydrolysing a 4-acetyl-alkoxy-7,7-dimethyl-3-oxabicyclo[4.1.0]-heptane having the formula II

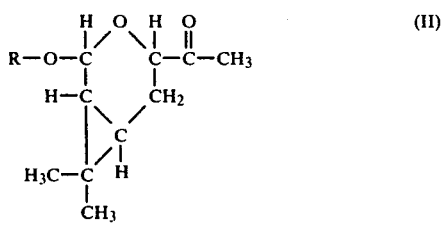

wherein R is an alkyl group containing less than 6, and preferably less than 3, carbon atoms. Compound II can exist, e.g., in the (1R,cis), and the (1S,cis) configuration regardless of the positions of the alkoxy and the acetyl groups with respect to the six-membered ring. A preferred starting material is 4-acetyl-2-methoxy-7,7-dimethyl-3-oxabicyclo[4.1.0]-heptane. The hydrolysis can easily be carried out in an aqueous acidic medium. Hydrolysis of acetals is described in, for example, "Methoden der organischen Chemie" (Houben-Weyl), Vol. VII, Part 1 (1954), pages 423–8. When starting from the (1R,cis) isomer of compound II, the process of the invention affords compound I exclusively in the (1R,cis) configuration.

The invention further provides the (1R,cis), (1R,trans) and (1S,trans) isomers of 1-(2-formyl-3,3-dimethylcyclopropyl)-3-oxo-2-butyl acetate having the formula III

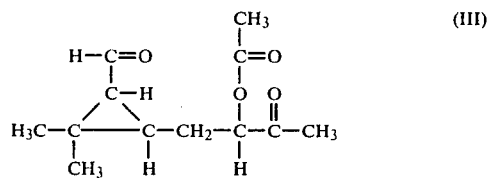

Compound III has two asymmetric carbon atoms in the cyclopropane ring and, therefore, may have the (1R,cis), (1R,trans), (1S,cis) or (1S,trans) configuration. The (1S,cis) isomer of this compound is described in *Tetrahedron,* 29 (1973), pages 403–12.

The invention also provides a process for the preparation of the (1R,cis), (1R,trans) or (1S,trans) isomers of 1-(2-formyl-3,3-dimethylcyclopropyl)-3-oxo-2-butyl acetate, which comprises reacting the (1R,cis), (1R,trans) or (1S,trans) configuration of 2-(2-hydroxy-3-oxo-butyl)-3,3-dimethylcyclopropanecarbaldehyde of formula I with a compound capable of converting an alcohol into the acetate of this alcohol. Suitable compounds capable of converting compound I into compound III are acetyl halides, particularly acetyl chloride. An acceptor for hydrogen halides is usually also present, for example, pyridine. Suitable methods for converting aldehydes are also described in "Methoden der organischen Chemie" (Houben-Weyl), Vol VIII (1952), pages 516–26 and 543–50. When starting from the (1R,cis) isomer of compound I, the process of the invention affords the compound of formula III exclusively in the (1R,cis) configuration.

The invention also provides a process for the preparation of 1-[2-(2,2-dihalovinyl)-3,3-dimethylcyclopropyl]-3-oxo-2-butyl acetate wherein each halo is independently chloro, fluoro or bromo, which process comprises two steps, the first step consisting in reaction of a tri-(dialkylamino)phosphine or an alkyl ester of an ortho-phosphorous acid bis(dialkylamide) with a compound generating a dihalocarbene—which reaction is allowed to proceed to virtual completion—and the second step consisting in reaction of the product resulting from the first step with 1-(2-formyl-3,3-dimethylcyclopropyl)-3-oxo-2-butyl acetate, both steps being carried out in the presence of a solvent.

Surprisingly, the two-step process according to the present invention affords 1-[2-(2,2-dihaloviryl)-3,3-dimethylcyclopropyl]-3-oxo-2-butyl acetate in a considerably higher yield than a one-step process comprising reaction of 1-(2-formyl-3,3-dimethylcyclopropyl)-3-oxo-2-butyl acetate, a tri(dialkylamino)phosphine or an alkyl ester of an ortho-phosphorous acid bis(dialkylamide), and a compound generating a dihalocarbene.

The alkyl groups present in the tri(dialkylamino)-phosphine or the alkyl ester of an ortho-phosphorous acid bis(dialkylamide) may be the same or different and linear or branched. The alkyl groups are suitably the same; they have preferably less than six, and more preferably less than three carbon atoms. The use of tri(dialkylamino)phosphines is preferred, because they usually afford 1-[2-(2,2-dihalovinyl)-3,3-dimethylcyclopropyl]-3-oxo-2-butyl acetate in a higher yield than the alkyl esters of ortho-phosphorous acid bis(dialkylamides) (the latter compounds are obtained by replacing one of the dialkylamino groups in a tri(dialkylamino)phosphine by an alkoxy group). Tri(diethylamino)phosphine and tri(-dimethylamino)phosphine are most preferred.

Tri(dialkylamino)phosphines may easily be prepared by reaction of a dialkylamine with a phosphorus trihalide, as described in "Organic Synthesis", Coll. Vol. V. (1973), pages 602-3. This reaction results in the formation of a solution of the tri(dialkylamino)phosphine which also contains precipitated dialkylammonium halide. Filtration of the precipitated dialkylammonium halide. Filtration of the precipitate and distillation of the filtrate yields a fraction of pure tri(dialkylamino)phosphine. Applicant has tried to avoid the preparation of pure tri(dialkylamino)phosphine by contacting the solution obtained after filtration of the precipitate, with 1-(2-formyl-3,3-dimethylcyclopropyl)-3-oxo-butyl acetate, but this procedure afforded only a very small amount of 1-[2-(2,2-dihalovinyl)-3,3-dimethylcyclopropyl]-3-oxo-2-butyl acetate, if any. It has now been found that this solution itself contains compounds which prevent the reaction with 1-(2-formyl-3,3-dimethylcyclopropyl)-3-oxo-2-butyl acetate and that these compounds can easily be removed. Accordingly, a preferred embodiment of the present invention comprises reacting a dialkylamine with a phosphorus trihalide in the presence of a solvent that is substantially inert, washing the resulting mixture with water (whether or not after prior separation of the precipitated dialkylammonium halide) and reacting the tri(dialkylamino) phosphine dissolved in the washed solution with the compound generating a dihalocarbene. This embodiment usually affords 1-[2-(2,2-dihalovinyl)-3,3-dimethylcyclopropyl]-3-oxo-2-butyl acetate in high yield. It is not necessary to separate the precipitated dialkylammonium halide prior to washing, because this salt is water-soluble. The yield of 1-[2-(2,2-dihalovinyl)-3,3-dimethylcyclopropyl]-3-oxo-2-butyl acetate can be further enhanced by drying the washed liquid, for example over a solid drying agent such as anhydrous sodium sulphate or anhydrous magnesium sulphate.

Another attractive feature of the process according to the present invention is that it may be carried out in the presence of alkane solvents, for example, in alkane solvents with a boiling point or boiling range up to 200° C. This also applies to the said reaction between a dialkylamine and a phosphorus trihalide. Examples of alkane solvents are pentane, hexane, heptane, octane and nonane. Mixtures of alkanes are very suitable, for example, gasolines having a boiling range from 60° C. to 82° C. to 110° C. If desired, the process may be carried out in substantially inert solvents other than alkanes, for example, in tetrahydrofuran or diethyl ether.

Examples of compounds generating a dihalocarbene under the conditions of the process according to the present invention are carbon tetrahalides, chloroform, bromoform and iodoform. Very good results have been obtained with carbon tetrahalides. Examples of carbon tetrahalides are carbon tetrachloride, carbon tetrabromide, carbon tetraiodide, bromotrichloromethane (forming dichlorocarbene) and dibromodifluoromethane (forming difluorocarbene). Very good results have been obtained with carbon tetrachloride.

Both steps of the process according to the present invention are preferably carried out at a temperature in the range of from −50° C. to +50° C., particularly at temperatures of from −20° C. to +35° C.

The process according to the invention may be carried out by adding a tri(dialkylamino)phosphine or an alkyl ester of an orthophosphorous acid bis(dialkylamide) to a compound generating a dihalocarbene, if desired, dissolved in a solvent that is substantially inert, for example, in an alkane solvent and stirring the mixture thus obtained until the first step has been substantially completed, which may take from 1 to 60 minutes. Then, 1-(2-formyl-3,3-dimethylcyclopropyl)-3-oxo-2-butyl acetate is added to the mixture and stirring continued for 1 to 60 minutes until the second step has been completed. Dihalophosphoranes and phosphine oxides can be removed from the reaction mixture by washing. This washing can be carried out with water when tri(dimethylamino)phosphine has been used, but when a tri(dialkylamino)phosphine having two or more carbon atoms in the alkyl groups has been used, dilute aqueous hydrochloric acid is more suitable than water. Therefore, tri(dimethylamino)phosphine is the most preferred tri(dialkylamino)phosphine. The washed reaction mixture is dried and the solvent is evaporated from the dried solution to leave a residue, which may be further purified, for example, by distillation, to give 1-[2-(2,2-dihalovinyl)-3,3-dimethylcyclopropyl]-3-oxo-2-butyl acetate in a pure state.

1-[2-(2,2-Dihalovinyl)-3,3-dimethylcyclopropyl]-3-oxo-2-butylacetate is a new chemical compound having the formula IV

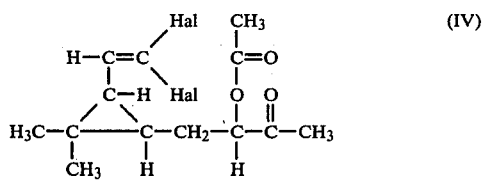

wherein each Hal independently is a chlorine, fluorine or bromine atom.

Compound IV has two asymmetric carbon atoms in the cyclopropane ring and, therefore, may have the (1R,cis), (1R,trans), (1S,cis) or (1S,trans) configuration. Each of the above-mentioned four spatial configurations exists in its own spatial configurations owing to the additional asymmetric carbon atom bound to the acetoxy group.

The invention also provides the compound 2-[2-(2,2-dihalovinyl)-3,3-dimethylcyclopropyl]ethylidene diacetate having the formula V

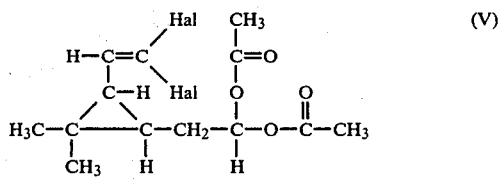

wherein each Hal independently is a chlorine, fluorine or bromine atom.

Compound V has two asymmetric carbon atoms in the cyclopropane ring and, therefore, may have the (1R,cis), (1R,trans), (1S,cis) or (1S,trans) configuration.

The invention also provides a process for the preparation of 2-[2-(2,2-dihalovinyl)-3,3-dimethylcyclopropyl]ethylidene diacetate wherein each halo independently is chloro, fluoro or bromo, which comprises oxidizing 1-[2-(2,2-dichlorovinyl)-3,3-dimethylcyclopropyl]-3-oxo-2-butyl acetate. The oxidation is suitably carried out with a peroxy acid, for example, perbenzoic acid, 3-chloroperbenzoic acid, peracetic acid, and perphthalic acid. Chloroform and acetic acid are suitable solvents. Oxidation of ketones with formation of esters is described in, for example, "Methoden der organischen Chemie" (Houben-Weyl), Volume VIII (1952), pages 449–60 and Volume VII/2b (1976), pages 1984–6. When starting from the (1R,cis) isomer of compound IV, the process according to the invention affords compound V exclusively in the (1R,cis) configuration.

The ethylidene diacetate is readily hydrolyzed, e.g., in the presence of acid, to yield 2-(2,2-dihalovinyl-3,3-dimethylcyclopropyl)ethanal as described in the concurrently filed U.S. patent application Ser. No. 55,855, now U.S. Pat. No. 4,222,964. This ethanal is treated with an alkanoic acid anhydride, e.g., in the presence of an amine, to yield a 2-(2,2-dihalovinyl-3,3-dimethylcyclopropyl)vinyl alkanoate which when oxzonized followed by oxidation decomposition yields free 2-(2,2-dihalovinyl)-3,3-dimethylcyclopropanecarboxylic acid as described in the concurrently filed U.S. patent application Ser. No. 55,858. These acids can be used to prepare pyrethroid esters, such as those described in U.S. Pat. No. 4,024,163.

ILLUSTRATIVE EMBODIMENTS

The present invention is illustrated by the following embodiments which describes the preparation of typical species of the invention and should not be regarded as limiting the invention in any way.

EMBODIMENT I

A 250-ml round-bottomed flask was charged with (1R,cis)-4-hydroxy-2-carene (77 mmol), (1R,cis)-4-hydroxy-7,7-dimethyl-3-methylene-bicyclo[4.1.0]heptane (55 mmol) and water-free methanol (50 ml). A mixture consisting of ozone and oxygen was passed through the liquid in the flask at a rate of 20 mmol of ozone per hour, while the temperature was maintained at 0° C. After 7.5 hours, no (1R,cis)-4-hydroxy-2-carene and (1R,cis)-4-hydroxy-7,7-dimethyl-3-methylenebicyclo[4.1.0]heptane could be detected in the flask. The reaction mixture was allowed to evaporated and the residue formed taken up in n-hexane (50 ml). The solution obtained was washed with two 25-ml portions of water and the washed solution was dried over anhydrous sodium sulphate. Evaporation of the solvent from the dried solution afforded a residue (22.85 g) which according to gas liquid chromatography analysis consisted of 4-acetyl-2-methoxy-7,7-dimethyl-3-oxabicyclo[4.1.0]heptane (100% (1R,cis), yield 96%, based on the starting amount of 4-hydroxy-2-carene) and 4-hydroxy-7,7-dimethylbicyclo[4.1.0]heptanone (100% (1R,cis), yield 97%, based on the starting amount of 4-hydroxy-7,7-dimethyl-3-methylenebicyclo[4.1.0]heptane). The residue was separated into its components by chromatography on basic alumina. 4-Acetyl-2-methoxy-7,7-dimethyl-3-oxabicyclo[4.1.0]heptane was eluted with n-hexane and 4-hydroxy-7,7-dimethylbicyclo[4.1.0]heptanone with diethyl ether. The Nuclear Magnetic Resonance spectrum of 4-acetyl-2-methoxy-7,7-dimethyl-3-oxabicyclo[4.1.0]heptane showed the following absorptions (using a solution of the compound in carbon tetrachloride and relative to a tetramethylsilane standard):

$\delta = 1.03$ ppm singlet, intensity 3, CH$_3$—C—CH$_3$
$\delta = 1.08$ ppm singlet, intensity 3, CH$_3$—C—C$\underline{H}_3$
$\delta = 1.30$–0.45 ppm multiplet, intensity 2, two H atoms bound to the cyclopropane ring
$\delta = 1.42$ ppm multiplet, intensity 1, CHC$\underline{H}_2$CH
$\delta = 1.95$ ppm multiplet, intensity 1, CHC$\underline{H}_2$CH
$\delta = 2.09$ ppm singlet, intensity 3 C(O)C$\underline{H}_3$
$\delta = 3.30$ ppm singlet, intensity 3, OC$\underline{H}_3$
$\delta = 3.78$ ppm two doublets, intensity 1, J=12 and 4 c/sec, OCH—C(O)
$\delta = 4.70$ ppm singlet, intensity 1, H$_3$COC$\underline{H}$ The 4-acetyl-2-methoxy-7,7-dimethyl-3-oxabicyclo[4.1.0]heptane had a purity of 98% and showed an $[\alpha]_D^{24} = 47.72$ (concentration 0.2 g/ml in benzene).

EMBODIMENT II
(1R,cis)-2-(2-hydroxy-3-oxobutyl)-3,3-dimethylcyclopropanecarbaldehyde A 50-ml flask was charged with 4-acetyl-2-methoxy-7,7-dimethyl-3-oxabicyclo[4.1.0]heptane prepared as in Embodiment I above (21.7 mmol, 100% (1R,cis)) and a 1:1 (v) mixture (10 ml) of acetic acid and water. After stirring of the contents of the flask for 5 hours at 20° C., water (30 ml) was added and the resulting mixture was extracted with two 25-ml portions of dichloromethane. The combined extract phases were washed with two 25-ml portions of a saturated aqueous solution of sodium hydrogen carbonate and then with a 10%w aqueous (25 ml) of sodium chloride. The washed organic phase was dried over anhydrous magnesium sulphate and the solvent was evaporated from the dried organic phase at 1.3 kPa to leave a residue (3.5 g) containing 2-(2-hydroxy-3-oxobutyl)-3,3-dimethylcyclopropanecarbaldehyde (100% (1R,cis), yield 88%.) The nuclear magnetic resonance spectrum of this desired product showed the following absorptions (using a solution of this product in deuterochloroform and relative to a tetramethylsilane standard):

$\delta = 1.24$ ppm singlet H$_3$C—C—CH$_3$
$\delta = 2.22$ ppm singlet H$_3$C—C=O
$\delta = 4.23$ ppm doublet of doublets $\underline{H}$C—OH
$\delta = 1.33$ ppm singlet H$_3$C—C—C$\underline{H}_3$
$\delta = 3.6$ ppm (variable) broad-O$\underline{H}$
$\delta = 9.69$ ppm doublet $\underline{H}$—C=O
multiplets for each of the H atoms bound to the ring.

EMBODIMENT III
(1R,cis)-2-(2-hydroxy-3-oxobutyl)-3,3-dimethylcyclopropanecarbaldehyde A 50-ml flask was charged with 4-acetyl-2-methoxy-7,7-dimethyl-3-oxabicyclo[4.1.0]heptane (10.1 mmol, 100% (1R,cis), a 1:1 (v) mixture (20 ml) of water and acetone and concentrated sulphuric acid (1.5 mmol), sp. gr. 1.84. After stirring the contents of the flask for one hour at 20° C. the majority of acetone was distilled off at 1.3 kPa. The residue was extracted with two 10-ml portions of dichloromethane. The combined extract phases were washed with two 20-ml portions of a saturated aqueous solutions of sodium hydrogen carbonate and then with a 10%w aqueous solution (20 ml) of sodium chloride. The washed organic phase was dried over anhydrous magnesium sulphate and the solvent was evaporated from the dried organic phase at 1.3 kPa to leave a residue (1.6 g) containing 2-(2-hydroxy-3-oxobutyl)-3,3-dimethylcyclopropanecarbaldehyde (100% (1R,cis), yield 86%).

EMBODIMENT IV
(1R,cis)-1-(2-formyl-3,3-dimethylcyclopropyl)-3-oxo-2-butyl acetate Acetyl chloride (30 mmol) was added with stirring over a period of 30 minutes and at a temperature between 5° and 10° C. to a 50-ml flask charged with 2-(2- hydroxy-3-oxobutyl)-3,3-dimethylcyclopropanecarbaldehyde (19.0 mmol, 100% (1R,cis), both spatial configurations around the C—OH present) prepared as in Embodiment III above, pyridine (60 mmol) and dichloromethane (20 ml). Then, consecutively, stirring was continued for 15 minutes, the temperature was allowed to raise to 20° C., water (20 ml) was added, the resulting mixture was acidified with concentrated aqueous hydrochloric acid (s.g. 1.19) to pH of 2, the acidified mixture was allowed to split up by settling into an aqueous and an organic phase and after separating off the aqueous phase, the organic phase was washed with two 30-ml portions of a 10%w aqueous solution of sodium chloride and a saturated aqueous solution (30 ml) of sodium hydrogen carbonate. The washed organic liquid was dried over anhydrous magnesium sulphate and the solvent was evaporated from the dried liquid at 1.3 kPa to leave a residue (3.3 g) containing 1-(2-formyl-3,3-dimethylcyclopropyl)-3,3-oxo-2-butyl acetate (100% (1R,cis), yield 77%). The nuclear magnetic resonance spectrum of this desired product showed the following absorptions (using a solution of this product in deuterochloroform and relative to a tetramethylsilane standard):

$\delta = 1.23$ ppm singlet $\underline{H}_3C$—C—$CH_3$
$\delta = 2.16$ ppm singlet $\underline{H}_3C$—C(O)—O—
$\delta = 5.07$ ppm doublet of doublets $H_2C$—C$\underline{H}$—O—
$\delta = 1.33$ ppm singlet $H_3C$—C—$\underline{C}H_3$
$\delta = 2.19$ ppm singlet $H_3C$—C(O)—C
$\delta = 9.63$ ppm doublet $\underline{H}$—C=O multiplets for each of the H atoms bound to the ring and for HC—C$\underline{H}_2$—CH.

EMBODIMENT V
(1R,cis)-1-[2-(2,2-dichlorovinyl)-3,3-dimethylcyclopropyl]-3-oxo-2-butyl acetate Tri(dimethylamino)phosphine (40 mmol) was added at −20° C. and with stirring under nitrogen to a 250-ml flask charged with carbon tetrachloride (40 mmol) and diethyl ether (160 ml). Then, the temperature was allowed to rise to +10° C. This finished the first step. The resulting suspension was cooled to −20° C. and a solution in diethyl ether (5 ml) of the (1R,cis) isomer of 1-(2-formyl-3,3-dimethylcyclopropyl-3-oxo-2-butyl acetate prepared as in Embodiment IV above was added. Then, the temperature of the mixture was allowed to rise to 20° C. This finished the second step. Water (50 ml) was added, the mixture was stirred for 5 minutes and, after settling, the organic phase was isolated and washed with two 50-ml portions of water. The washed organic liquid was dried over anhydrous magnesium sulphate and the solvent was evaporated from the dried liquid at 1.3 kPa to leave a residue (3.5 g) containing 1-[2(2,2-dichlorovinyl)-3,3-dimethylcyclopropyl]-3-oxo-2-butyl acetate (100% (1R,cis), yield 84%).

The NMR spectrum of this desired product showed the following absorptions (using a solution of this product in deuterochloroform and relative to a tetramethylsilane standard):

$\delta = 1.04$ ppm singlet $\underline{H}_3C$—C—$CH_3$
$\delta = 2.19$ ppm singlet $H_3C$—C(O)—C and $\underline{H}_3C$—C-(O)—O—
$\delta = 5.05$ ppm doublet of doublets $H_2C$—C$\underline{H}$—O—
$\delta = 1.16$ ppm singlet $H_3C$—C—$\underline{C}H_3$
$\delta = 5.59$ ppm doublet $\underline{H}C=CCl_2$ multiplets for each of the H atoms bound to the ring and for HC—C$\underline{H}_2$—CH.

EMBODIMENT VI (1R,cis)-1-8
2-(2,2-dichlorovinyl)-3,3-dimethylcyclopropyl]-3-oxo-2-butyl acetate Tri(dimethylamino)phosphine (40 mmol) was added with stirring at −20° C. to a solution of 1-(2-formyl-3,3-dimethylcyclopropyl)-3-oxo-2-butyl acetate (14.2 mmol) and carbon tetrachloride (40 mmol) in diethyl ether (160 ml) kept under nitrogen. Then, the temperature of the mixture was allowed to rise to 20° C. Water (50 ml) was added, the mixture was stirred for 5 minutes and, after settling, the organic phase was isolated. The organic phase was washed with two 50-ml portions of water. The washed organic phase was dried over anhydrous magnesium sulphate and the solvent was evaporated from the dried solution to leave a residue (2.2 g) containing 1-[2-(2,2-dichlorovinyl)-3,3-dimethylcyclopropyl]-3-oxo-2-butyl acetate (100% (1R,cis), yield 54%).

EMBODIMENT VII
(1R,cis)-2-[2-(2,2-dichlorovinyl)-3,3-dimethylcyclopropyl]ethylidene diacetate The contents of a 50-ml flask charged with 1-[2-(2,2-dichlorovinyl)-3,3-dimethylcyclopropyl]-3-oxo-2-butyl acetate prepared as in Embodiment VI above (11.9 mmol, 100% (1R,cis) both spatial configurations around $\underline{C}$—C(O)CH$_3$ present), chloroform (10 ml) and 3-chloroperbenzoic acid (26 mmol) were stirred magnetically for five hours at 20° C. Then, another quantity of 3-chloroperbenzoic acid (6 mmol) was added and stirring was continued for 16 hours. The reaction mixture obtained was continued for 16 hours. The reaction mixture obtained was mixed with dimethyl sulphide (2 ml), keeping the temperature at 20° C., stirring was continued for 15 minutes, dichloromethane (30 ml) was added, the suspended material was filtered off, the filtrate was washed with two 20-ml portions of a saturated aqueous solution of sodium hydrogen carbonate and two 20-ml portions of a 10%w aqueous solution of sodium chloride. The washed organic phase was dried over anhydrous magnesium sulphate and the solvent was evaporated (2 kPa) from the dried liquid to leave a residue (2.3 g) containing the desired (100% (1R,cis), yield 63%). The nuclear magnetic resonance spectrum of this product showed the following absorptions (using a solution of this product in deuterochloroform and relative to a tetramethylsilane standard):

$\delta = 1.05$ ppm singlet $\underline{H}_3C$—C—$CH_3$
$\delta = 1.15$ ppm singlet $H_3C$—C—$\underline{C}H_3$
$\delta = 2.12$ ppm singlet both $\underline{H}_3C$—C(O)—O—
$\delta = 5.62$ ppm doublet $\underline{H}C=CCl_2$
$\delta = 6.86$ ppm triplet $\underline{H}$—C—O— multiplets for each of the H atoms bound to the ring and for HC—C$\underline{H}_2$CH.

I claim:

1. 1-[2-(2,2-dihalovinyl)-3,3-dimethylcyclopropyl]-3-oxo-2-butyl acetate wherein each halo is independently chloro, fluoro or bromo.

2. An acetate according to claim 1 wherein each halo is chloro.

3. The (1R,cis) isomer of the compound claimed in claim 2.

* * * * *